(12) United States Patent
Irion et al.

(10) Patent No.: US 6,251,108 B1
(45) Date of Patent: *Jun. 26, 2001

(54) SMOOTH-SURFACE ROTARY ELECTRODE FOR HF SURGERY

(75) Inventors: Klaus Irion, Liptingen (DE); Simon Solingen, Los Angeles, CA (US)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,719
(22) PCT Filed: Jun. 24, 1997
(86) PCT No.: PCT/DE97/01310
§ 371 Date: Dec. 21, 1998
§ 102(e) Date: Dec. 21, 1998
(87) PCT Pub. No.: WO97/49346
PCT Pub. Date: Dec. 31, 1997

(30) Foreign Application Priority Data

Jun. 24, 1996 (DE) .............................. 196 25 242

(51) Int. Cl.[7] .................................................. A61B 18/18
(52) U.S. Cl. ............................... 606/41; 606/46; 600/374
(58) Field of Search ................................... 606/41, 42, 45, 606/46, 48–50; 600/374

(56) References Cited

U.S. PATENT DOCUMENTS

| 4,917,082 | * | 4/1990 | Grossi et al. | 606/46 |
| 5,462,545 | * | 10/1995 | Wang et al. | 606/41 |
| 5,549,605 | * | 8/1996 | Hahnen | 606/46 |
| 5,634,924 | * | 6/1997 | Turkel et al. | 606/46 |
| 5,713,895 | * | 2/1998 | Lontine et al. | 606/41 |
| 5,827,274 | * | 10/1998 | Bonnet et al. | 606/41 |
| 5,836,875 | * | 11/1998 | Webster, Jr. | 600/374 |
| 5,908,419 | * | 6/1999 | Hahnen et al. | 606/46 |
| 5,980,520 | * | 11/1999 | Vancaillie | 606/49 |

* cited by examiner

Primary Examiner—Michael Peffley
(74) Attorney, Agent, or Firm—St.Onge Steward Johnston & Reens LLC

(57) ABSTRACT

What is described here is an electrode for HF surgery and especially for vaporizing tissue, comprising at least one electrode body which comes into contact with the tissue to be treated at least in parts, at least one lead via which the electrode body is connected to an HF supply unit. The invention is characterized by the provisions that each electrode body presents a smooth surface in that zone which comes into contact with the tissue, in which smooth surface regions of low electrical conductivity and a plurality of regions of high electrical conductivity are electrically interconnected, at least in parts.

8 Claims, 2 Drawing Sheets

SMOOTH-SURFACE ROTARY ELECTRODE FOR HF SURGERY

The present invention relates to an electrode for HF surgery, and specifically an electrode for vaporising tissue.

BACKGROUND OF THE INVENTION

Many treatment jobs require electrodes which are suitable for being rolled over the tissue so as to achieve a homogeneous success of treatment over a major area:

From the German Patent DE 42 42 126 C1, for instance, an electrode for HF surgery has become known. That known electrode comprises a body of revolution which presents projections on its surface which sink into the endometrium and which are specifically configured in the form of spikes. As a result of the projections on the body of rotation, which sink into the tissue, the greatest current density is intended to be achieved in the depth of the tissue rather than on the surface.

Similar electrodes are known from the U.S. Pat. No. 5,395,363 or from the laid-open German Patent Application DE-OS 22 22 820.

In a number of cases, however, a penetration of the electrode body into the tissue is undesirable. In another HF surgery electrode of the claimed general type, the electrode body is therefore provided with recesses rather than projections so that a specific current distribution is achieved even though the electrode does not sink into the tissue on account of these recesses. In this respect reference is made to the German Utility Model DE 295 11 618 U1.

With this configuration, however, disadvantages are entailed in practical application, such as a higher risk of injury due to the shoulders or recesses in which tissue fragments could "get caught".

The invention is therefore based on the problem of providing an electrode for HF surgery, and particularly for vaporising tissue, which comprises an electrode body rolling over the tissue and suitable to achieve a certain distribution of current density without occurrence of the disadvantages linked up with the use of projections or recesses, respectively.

One inventive solution to this problem is solved by an electrode having its body formed with a plurality of regions with high and low electrical conductivity which constitute a smooth surface of the body.

The invention deviates from the obviously generally prevailing view about electrodes of the claimed general type, which comprise at least one rolling electrode body, that merely an electrode body provided with projections or recesses could ensure the desired distribution of current flow and hence the desired success of the treatment.

In accordance with the invention an electrode is provided which comprises at least one electrode body rolling over the tissue and having a smooth surface in contact with the tissue, which is smooth. In the smooth surface regions of low electrical conductivity or insulating regions and a plurality of regions which are not coherent in the surface, which present a high electrical conductivity. The regions of high electrical conductivity may be combined to form one or several groups, with the regions of each group being interconnected inside the electrode body or outside the electrode body in an electrically conducting way.

The connection may be made in such a form that all the regions are interconnected—which means that only one group is provided—so that an electrode operating in a monopolar way is obtained.

It is moreover possible that the electrically conducting regions are combined to form at least two groups interconnected each inside the electrode body so that the electrode presenting such an inventive structure may be employed as bipolar electrode.

In accordance with a further aspect of the invention the regions of low electrical conductivity are preferably made of an electrically insulating material.

Since the individual regions account for a defined share of the surface it is possible to adjust a defined distribution of current density.

A further aspect of the invention discloses the electrode body comprising an electrically conducting central region having projection extending towards the smooth surface which comes into contact with the tissue. The areas between the projections are filled with a material of low electrical conductivity or with insulating properties, respectively, so that the smooth surface employed in accordance with the invention is achieved. The surface regions with a good electrical conductivity or with insulating properties, respectively, may be arranged with a statistic distribution or in a regular array. Which of the two possibilities is actually selected depends on the respective medical application.

In the event of regularly arranged projections the central region may present longitudinal and/or transverse grooves and/or projections extending towards the smooth surface, depending on the medical indication of the respective different possibilities and/or on the least complex production possible in terms of manufacturing engineering.

In any case, however, it is preferred that the entire planar extension of the regions with good electrical conductivity is smaller than the extension of the regions with poor electrical conductivity because with such a configuration a distribution of the current density is achieved which is particularly well suitable for vaporisation.

The fundamental idea of the inventions is to use an electrode body with a smooth surface in which merely one part of the surface contributes to the flow of current and may be applied to different electrodes.

The electrode body may, for instance, present the shape of a cylinder or of a ball, which parts are supported for rotation so that the electrode may be moved over the tissue in a rolling motion, and it may be applied to electrode bodies presenting the shape of a plate or a tape which is bent in at least one direction.

The safety for the patient is increased by utilizing the material of low electrical conductivity or with insulating properties, respectively, connected by a positive connector to the central electrode body so as the risk is reduced that some detached material may deposit in the body.

According to still another aspect of the invention, a method for making an electrode having a smooth surface which is provided with a different electrical conductivity is also provided.

The method of producing an electrode, initially an electrode body is manufactured which presents at least one electrically conducting region, in which recesses are formed in that surface region which comes into contact with the tissue to be treated. The recesses are filled with a material of poor electrical conductivity so that a smooth surface is created. To this end a coating process or a vapour deposition process may be employed. After the recesses have been filled the electrode may be machined, for instance, at least in that part of the surface which comes into contact with the tissue to be treated. This produces a defined surface which is smooth in correspondence with the selected machining operation.

Still another aspect of the invention describes undercuts which are provided in the recesses in the electrode body so that the material of low electrical conductivity will adhere to the electrode body in a positive locking action. This enhances the safety level for the patient—as has been set out above. In any case, the inventive configuration of the electrode body leads to surprising advantages over both the common rolling electrode bodies with projections or recesses and electrode bodies in a rigid arrangement and having a smooth surface with regions of different conductivity, which are distributed in the surface—in this respect reference is made to the U.S. Pat. No. 3,460 539: Compared to this prior art a particularly homogeneous and efficient application of HF current to the tissue is achieved due to the rolling motion of the smooth surface, including areas of different conductivity, on the tissue.

BRIEF DESCRIPTION OF THE DRAWINGS

The invention will be described in more details by an exemplary embodiment in the following, with reference to the drawing wherein.

DETAILED DESCRIPTION

Figure 1A:
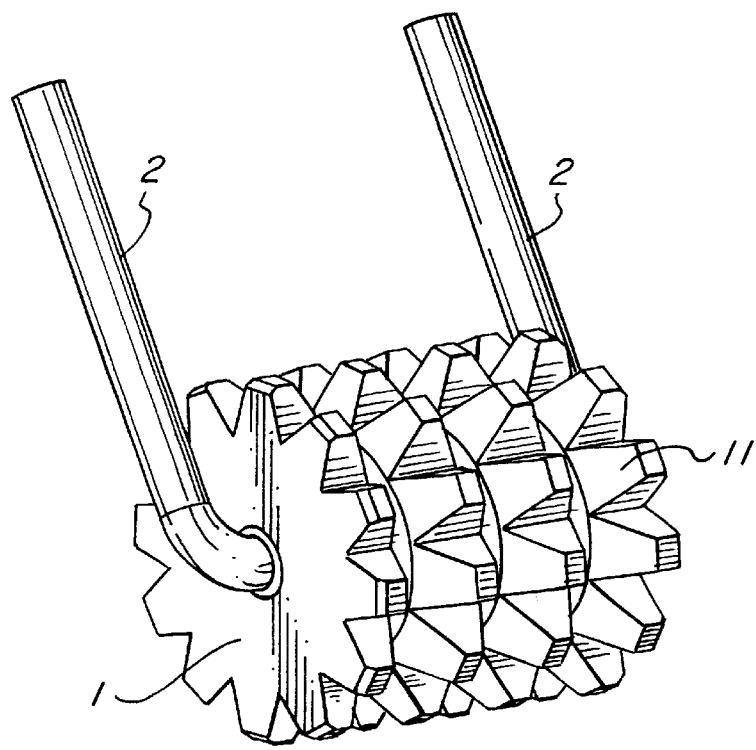
FIG. 1a shows the electrode body of a first embodiment of the invention.

FIG. 1 shows an electrode body 1 of an HF electrode for HF surgery which is suitable for monopolar operation, especially for vaporising tissue. The electrode body 1 comprises two leads 2 via which it is connected to one pole of an HF supply unit (not illustrated here). In the embodiment shown in this Figure the electrode body 1 is a cylinder supported for rotation, which presents projections 11 on its surface. The electrode body consists of an electrically conducting material of a type commonly used for the production of HF electrodes.

What is not shown in the Figures is the guiding element which may be configured in a manner known per se, e.g. from the U.S. Pat. No. 5,395,363 or in a form known from endoscopy.

Figure 1B:
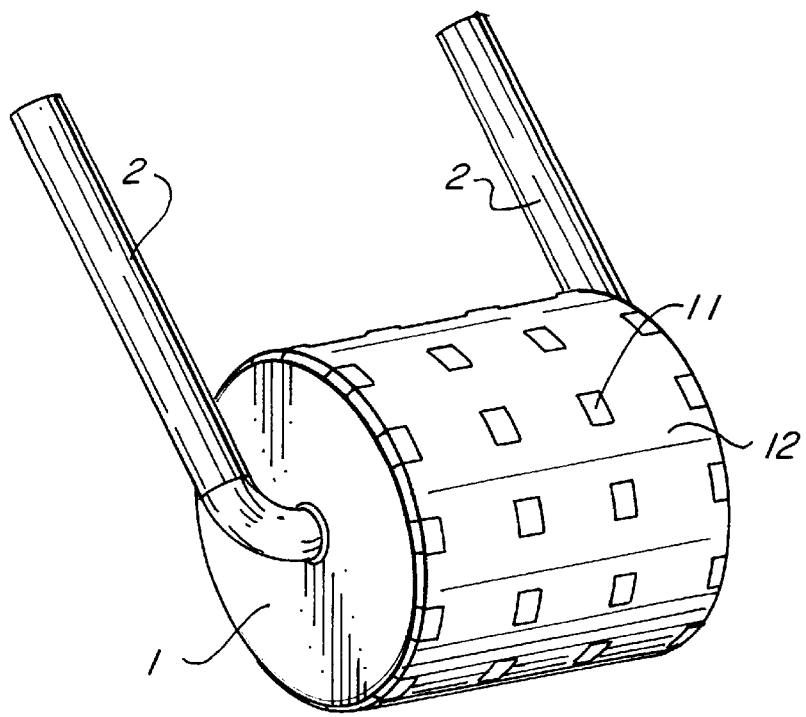
FIG. 1b is a view of the complete electrode of this embodiment.

FIG. 1b shows the complete electrode in which the recesses between the projections 11 are so filled with an electrically insulating material 12 that the surface of the electrode body 1 is a smooth cylinder surface.

The electrode may hence be moved over the tissue in a rolling motion, without sinking into the tissue or without any risk of injury or the risk of tissue fragments caught in the recesses.

Figure 2:
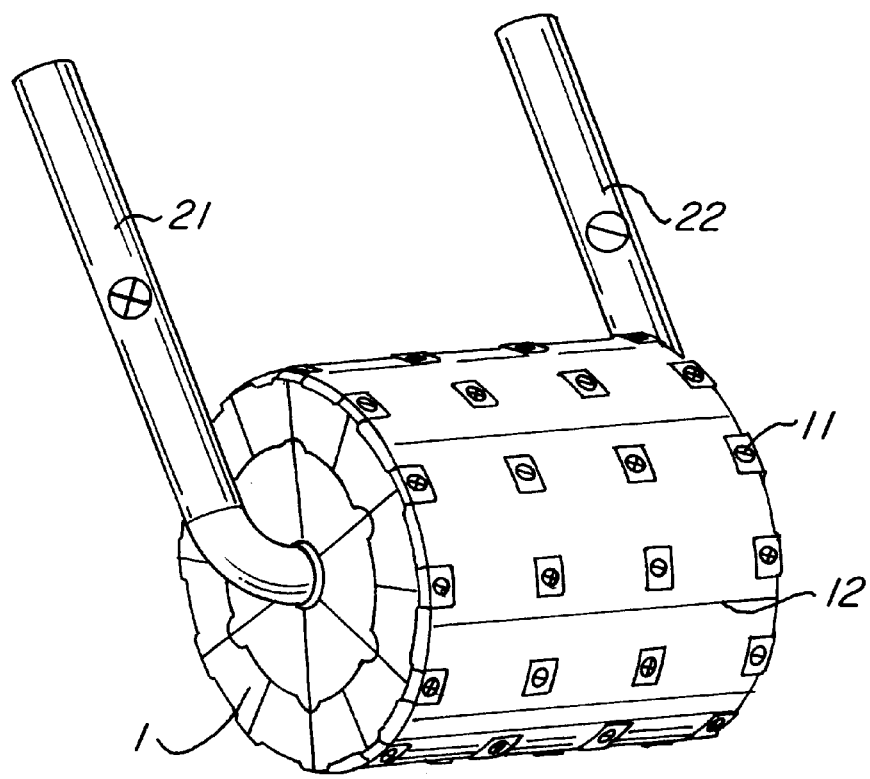
FIG. 2 illustrates the electrode of a second embodiment of the invention.
Figure 2A:
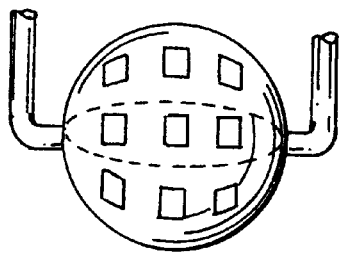
FIG. 2a illustrates the electrode of a third embodiment of the invention.
Figure 3:
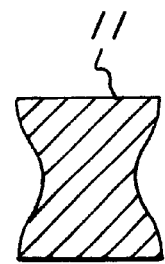
FIG. 3 is a view of the undercut used to secure the inserts.

FIG. 2 is an illustration of an embodiment of the invention where the electrode is of the bipolar type. For implementation of a bipolar electrode the lead 21 is connected to one pole of an HF supply unit, which is not shown here, whilst the lead 22 is connected to the other pole of the HF supply unit. In correspondence with this configuration two groups of projections 11 are provided in the surface of the electrode body 1, of which one group is connected to the lead 21 whilst the other group is electrically connected to the lead 22. This is roughly indicated by the minus or plus signs in the individual projections 11. The space between the projections 11 in its turn is filled with an electrically insulating material 12.

When the electrode body 1 is now moved over the tissue to be treated in a rolling motion a current flow occurs over the tissue between the projections 11 connected to the lead 21 and the projections connected to the lead 22.

The invention has been described in the foregoing with reference to embodiments without any restriction of the general inventive idea.

What is claimed is:

1. An electrode for use in HF surgery comprising:
a body having an axis of rotation and having a continuous outer surface of low electrical conductivity, said body having opposite axially spaced apart ends;
a pair of leads, each having respective distal and proximal ends, the distal ends of the leads supporting the opposite ends of the body so as to rotate the body about the axis of rotation;
an HF supply unit operatively connected to the proximal ends of the leads; and
a multiplicity of electro-conductive inserts recessed in the body and spaced circumferentially and axially from one another, said inserts having outer surfaces flush with the surface of the body to form a roller with the body, at least a part of the inserts being connected to one of the leads.

2. The electrode defined in claim 1, wherein the body is selected from the group consisting of a cylinder and a ball, the outer surfaces of the inserts cumulatively composing up to 20% percent of the entire surface of the body.

3. The electrode defined in claim 1, wherein the entire multiplicity of the inserts are connected to the one lead, so that the electrode is a monopolar electrode.

4. The electrode defined in claim 1, wherein the remaining inserts are connected to the other lead, so that the electrode is a bipolar electrode.

5. An electrode for use in HF surgery comprising:
a rotary electrically conductive body having an axis of rotation and a pair of diametrically spaced apart ends;
a multiplicity of identical pyramidal projections extending outwardly in respective annular rows axially spaced across the body between the ends, each of said projections having a respective outer face;
an electrically insulating material filling spaces between said projections and forming a surface of revolution flush with the outer faces of the projections to form a roller with the body; and
a support having a distal end rotatably supporting the roller.

6. The electrode defined in claim 5, wherein the faces of the inserts having the same straight line generatrix as the surface of the body.

7. The electrode defined in claim 5, wherein the body has a plurality of recesses receiving the inserts, each of the recesses having a respective undercut engaging the insert for a positive locking effect.

8. A method for producing an electrode for use in HF surgery, comprising the steps of:
providing an electro-conductive body having an axis of rotation and a pair of axially spaced apart ends;
providing a multiplicity of annular rows of identical pyramidal projections spaced axially from one another and having outer faces, thereby forming a plurality of spaces between the projections;
filling the spaces with an electrically insulating material to form a surface of revolution flush with the outer faces of the projections to form a roller with the body; and
rotatably supporting the roller with a distal end of a support.

* * * * *